United States Patent

Arena et al.

Patent Number: 5,258,558
Date of Patent: Nov. 2, 1993

[54] DIRECT CONVERSION OF BUTYRALDEHYDE TO 2-ETHYLHEXANOL-1

[75] Inventors: Blaise J. Arena, Des Plaines; Jennifer S. Holmgren, Bloomingdale, both of Ill.

[73] Assignee: UOP, Des Plaines, Ill.

[21] Appl. No.: 884,000

[22] Filed: May 18, 1992

Related U.S. Application Data

[63] Continuation-in-part of Ser. No. 779,755, Oct. 21, 1991.

[51] Int. Cl.$^5$ ............... C07C 29/141; C07C 29/14
[52] U.S. Cl. ............................. 568/881; 568/463; 568/850; 568/880
[58] Field of Search ............... 568/840, 876, 878, 880, 568/881, 463

[56] References Cited

U.S. PATENT DOCUMENTS

| | | | |
|---|---|---|---|
| 3,991,127 | 11/1976 | Corr et al. | 568/881 |
| 4,138,588 | 2/1979 | Tummes et al. | 568/881 |
| 4,532,351 | 7/1985 | Barnett et al. | 568/881 |
| 4,837,368 | 6/1989 | Gustafson et al. | 568/881 |
| 5,120,853 | 6/1992 | Yoneyoshi et al. | 568/880 |

OTHER PUBLICATIONS

Nakatsuka et al., *Bull. Chem. Soc. Japan*, 52, 2449 (1979).
W. T. Reichle, *J. of Catalysis*, 94, 546 (1985).
E. Suzuki and Y. Ono, *Bull Chem. Soc., Japan*, 61, 1008 (1988).
Nunan et al., *J. of Catalysis*, 116 222 (1989).
A. Corma and coworkers, *Applied Catalysis*, 59, 237 (1990).
A. Corma and R. N. Martin-Aranda, *J. Catalysis*, 130, 130 (1991).
M. Komiyama, *Catalysis Reviews, Science and Engineering*, vol. 27 341 (1985).

Primary Examiner—Werren B. Lone
Attorney, Agent, or Firm—Thomas K. McBride; Eugene I. Snyder

[57] ABSTRACT

Solid solutions of magnesium oxide-aluminum oxide related to hydrotalcite and what previously has been referred to as synthetic hydrotalcites, have been prepared with a surface area in excess of 250 m$^2$/g, especially at low Mg/Al atom ratios. Such high surface area materials are found to be quite effective in the aldol condensation of aldehydes, and in particular in the conversion of n-butyraldehyde to 2-ethyl-2-hexenal in high yield and with good selectivity in a liquid phase reaction at temperatures under about 200° C.

20 Claims, No Drawings

DIRECT CONVERSION OF BUTYRALDEHYDE TO 2-ETHYLHEXANOL-1

CROSS-REFERENCE TO RELATED APPLICATION

This application is a continuation-in-part of my copending application, Ser. No. 779,755, filed Oct. 21, 1991, all of which is hereby incorporated by reference.

BACKGROUND OF THE INVENTION

The world-wide production of 2-ethylhexanol-1, which is prepared from 2-ethyl-2-hexenal, is greater than all alcohols other than those containing from 1 to 4 carbon atoms, due mainly to the widespread use of its carboxylic acid esters as a plasticizer, especially in polyvinylchloride. Other uses of this 8-carbon alcohol include the production of intermediates for acrylic surface coatings, diesel fuel and lube oil additives, and surfactants. 2-Ethylhexanol-1 is prepared from n-butyraldehyde as the feedstock, where the latter is the highest volume oxide chemical produced, via the aldol condensation of n-butyraldehyde to 2-ethyl-2-hexenal followed by reduction of both the olefin and aldehyde moieties.

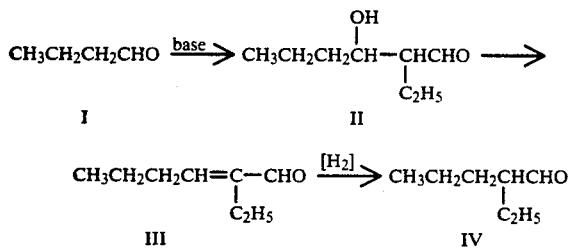

where the actual aldol condensation is represented by the conversion I to II.

The aldol condensation of aldehydes is a well known and time honored reaction employed for many years in the production of several commercially important materials in addition to 2-ethylhexanol-1, for example, the formation of isophorone and mesitylene oxide from acetone. The reaction is not merely base catalyzed, but usually needs a strong base catalyst in order to proceed satisfactorily. Although the aldol product corresponding to II may often be isolated, its dehydration to III is usually facile under the reaction conditions, and accordingly it is the alpha, beta-unsaturated aldehyde III which generally is the isolated reaction product.

Often the strong bases used as catalysts in aldol condensation are the alkali metal hydroxides, especially under aqueous or partly aqueous conditions. It should be apparent that the use of strong bases does not lend itself to the adaptation of aldol condensation as a continuous process, in large part because of their having unfavorable properties when used as a fixed bed. Yet development of a continuous process for the production of 2-ethyl-2-hexenal and other aldol condensation products is not merely of great interest but rather is of high priority, because of the well-known advantages of fixed bed continuous processes generally and because it would minimize environmental problems associated with the disposal of a strong base as well as minimizing corrosion difficulties caused by a strong aqueous base.

The desirability of a strong base suitable for use as a fixed bed previously has been recognized and has led to the use of such materials, inter alia, of sodium on alumina and potassium on graphite. Because of the severe limitations of such strong bases in a fixed bed, more recent attention has turned to clays and clay-like materials as suitable alternatives.

Before proceeding it appears advisable to prevent semantic obfuscation by defining several terms. Although "hydrotalcite" is most properly applied to a clay of composition $Mg_6Al_2(OH)_{16}(CO_3) \cdot 4H_2O$ often it has been used to describe related layered double hydroxides with varying Mg/Al ratios. However, at least when the number ratio of Mg/Al atoms is less than 3, after calcination such materials are better described as solid solutions of magnesium oxide and aluminum oxide. That is, calcination destroys the layered structure characteristic of hydrotalcite and affords a solid solution. But the terminology as applied to such solid solutions often retains the "hydrotalcite" name, as in, for example, "synthetic hydrotalcites". In this application henceforth we shall try to be consistent in using the term "solid solution of magnesium oxide and aluminum oxide" to describe such calcined synthetic materials. The second point involves the use of the term "Mg/Al". In this application Mg/Al shall be the number ratio of magnesium to aluminum atoms in a solid solution of magnesium oxide and being derived from hydrotalcite itself. In one series of catalysts the carbonate moiety of hydrotalcite was exchanged by $NO_3^{2-}$, $SO_4^{2-}$, or $CrO_4^{2-}$, and in the other series there was isomorphous substitution of $Mg^{2+}$—$Al^{3+}$ by $Li^+$—$Al^{3+}$, $Co^{2+}$—$Al^{3+}$, $Ni^{2+}$—$Al^{3+}$, or $Zn^{2+}$—$Cr^{3+}$. At 500° C. reaction temperature none of the foregoing appeared to lead to increased acetone conversion although some slight increase in selectivity (especially at lower conversion) was observed. Nunan et al., *J. of Catalysis*, 116, 222 (1989), has prepared related materials by isomorphous substitution of Mg by Cu and Zn, and of Al by Cr or Ga.

Before proceeding it appears advisable to prevent semantic obfuscation by defining several terms. Although "hydrotalcite" is most properly applied to a clay of composition $Mg_6Al_2(OH)_{16}(CO_3) \cdot 4H_2O$ often it has been used to describe related layered double hydroxides with varying Mg/Al ratios. However, at least when the number ratio of Mg/Al atoms is less than 3, after calcination such materials are better described as solid solutions of magnesium oxide and aluminum oxide. That is, calcination destroys the layered structure characteristic of hydrotalcite and affords a solid solution. But the terminology as applied to such solid solutions often retains the "hydrotalcite" name, as in, for example, "synthetic hydrotalcites". In this application henceforth we shall try to be consistent in using the term "solid solution of magnesium oxide and aluminum oxide" to describe such calcined synthetic materials. The second point involves the use of the term "Mg/Al". In this application Mg/Al shall be the number ratio of magnesium to aluminum atoms in a solid solution of magnesium oxide and aluminum oxide. While this definition has been previously employed by, for example, Reichle, others have used a different definition for the Mg/Al ratio.

Shortly after Reichle's work, Corma and coworkers described their investigations into the use of certain zeolites as base catalysts; A. Corma and coworkers, *Applied Catalysis*, 59, 237 (1990). The effect of a series of alkali metal exchanged X and Y zeolites was investigated in batch reactions in catalyzing the condensation of benzaldehyde with ethylcyanoacetate and diethyl malonate, where it was determined that the reactivity of the metal-exchanged zeolites was in the order cesium->potassium>sodium>lithium, and X>Y. The $pK_b$'s of these materials were said to be between about 10.3 and 13, which is far less than that given by Reichle for his "synthetic hydrotalcites". In related work [A. Corma and R. N. Martin-Aranda, *J. Catalysis*, 130, 130 (1991)], Corma exchanged the magnesium ions on the edges of the octahedral sheet in sepiolite with alkali metal ions to afford materials also effective as base catalysts in the foregoing condensation, but noted that the basicity of the resulting materials also was far less than that of hydrotalcite.

Our objective was the development of a process for the production of 2-ethyl-2-hexenal via the continuous aldol condensation of n-butyraldehyde, especially in the liquid phase. It was important that the process be continuous and employ a fixed bed of catalyst. Therefore the catalyst had to possess suitable flow properties, compressibility, and so forth, consistent with a liquid flow. It is important to note that whereas aldol condensation of n-butyraldehyde is generally performed in the vapor phase, it was quite desirable that the new process also be applicable to liquid phase aldol condensation. It also is important that the aldol condensation of n-butyraldehyde proceed in relatively high yield, with good selectivity, and at modest temperatures, say less than 200° C. Since water is a reaction product, it is important that the catalysts exhibit hydrothermal stability. Although solid solutions of magnesium oxide and aluminum oxide previously have been used for the gas phase aldol condensation of n-butyraldehyde, the described materials were found inadequate for our process. In contrast, we have prepared solid solutions of magnesium oxide and aluminum oxide with unusually high surface area and with relatively low Mg/Al ratios, which appear to satisfy the foregoing criteria in all respects.

SUMMARY OF THE INVENTION

The purpose of this invention is to develop a continuous process for the preparation of 2-ethyl-2-hexenal by the aldol condensation of n-butyraldehyde using a fixed bed of basic catalyst, especially where the process is applicable also to a liquid phase condensation. One embodiment comprises passing n-butyraldehyde over a fixed bed of a solid solution of magnesium oxide and aluminum oxide having a surface area greater than 250 m$^2$/g. In a more specific embodiment the solid base catalyst has a surface area between 250 and 350 m$^2$/g. In a still more specific embodiment the magnesium oxide-aluminum oxide solid solution has a Mg/Al number atom ratio between about 1.5 and 2.5. In another specific embodiment the reaction temperature is between about 80° and about 200° C. Other variants and embodiments will be apparent from the ensuing description.

DESCRIPTION OF THE INVENTION

Our invention is based on the observation that magnesium oxide-aluminum oxide solid solutions having a surface area between about 250 and about 350 m$^2$/g are quite effective in promoting the aldol condensation of aliphatic aldehydes, and especially n-butyraldehyde, with both high conversion and high selectivity at temperatures under 200° C. This observation affords the opportunity to devise a continuous process for the preparation of the aldol condensation products of these aldehydes, and in particular for the preparation of 2-ethyl-2-hexenal, the dehydrated aldol condensation product of n-butyraldehyde, whether the process be a vapor or liquid phase condensation.

The aldehydes used as feedstocks in the practice of this invention have the formula R—CH$_2$CHO. In one variant R is an alkyl or alkenyl moiety, either linear or branched, having from 1 to 20 carbon atoms. Variants where R has from 1 to 10 carbon atoms are preferred, and those where R has between 2 and 4 carbon atoms are even more desirable. Although R may be an alkenyl moiety, the variant where R is a saturated alkyl moiety is the more usual one, and the most usual case is that where R is a linear, saturated alkyl group having between 2 and 4 carbon atoms. The case where R is an ethyl group, i.e., the aldehyde is n-butyraldehyde, is especially preferred.

In another variant R is an aralkyl moiety whose alkyl portion is linear with a carbon number from 1 through 20, and especially having from 1 to 10 carbon atoms in the alkyl chain. The aryl group may be anywhere on the alkyl chain; its position is in no way restrictive. That variant where the aryl group is phenyl is the most common one, although substituted phenyl and higher aromatic systems, such as naphthyl, anthryl, phenanthryl, biphenylyl, and so forth, may be used without prejudice. As will be emphasized below the continuous aldol condensation often is most desirably performed in the liquid phase, therefore in this modification whatever aldehyde is used flows through a fixed catalyst bed in the liquid phase.

The novel base catalyst employed in our invention is a solid solution of magnesium oxide and aluminum oxide, MgO and Al$_2$O$_3$, having a surface area between 250 and 350 m$^2$/g. It is preferable that the MgO/Al$_2$O$_3$ solid solution has a surface area at least about 275 m$^2$/g and even more preferable that it be in the range from 300 to 350 m$^2$/g. Although the unusually high surface area of the magnesia-alumina solid solutions appears to be the most important property related to the unique functional characteristics of the catalysts of our invention, we also have a strong preference that our unique catalysts have a Mg/Al atom number ratio between about 1.5 and 2.5, which is on the low end of Mg/Al ratios for the solid solutions of interest. We have found that such catalysts afford excellent conversion of the aldehyde to its aldol condensation product with good selectivity throughout a wide range of conversion at quite reasonable liquid hourly space velocities, or productivity.

The solid basic catalysts of our invention with their unique properties result from an atypical preparation of these materials. In particular, as described in more detail within, the precursor gel is prepared at a temperature not exceeding about 10° C., and preferably is prepared in the temperature interval between about 0° and 5° C. In addition, the crystallization time is kept short, on the other of an hour or two at 65° C., and affords material of unusual hydrothermal stability. This is evidenced by the fact that spinel formation is not seen until calcination temperatures of about 800° C., whereas in the prior art material the spinel phase begins to appear at a calcination temperature of about 600° C. In addition, the solid basic catalysts of our invention show greater product homogeneity as evidenced by their resistance to spinel formation. The increased hydrothermal stability of our solid basic catalyst is important since water is generally one of the reaction products accompanying aldol condensation, and although the reaction does not proceed in an aqueous solution, where hydrothermal stability is most important, the catalyst is continually exposed to significant concentrations of water.

The aldol condensation of the aldehydes of this invention are carried at a temperature between about 80° and about 200° C., and most commonly between about 100° and 190° C. Where a liquid phase reaction is desired, the reaction pressure is important only insofar as ensuring that the reaction occur in the liquid phase. So, for example, to ensure a liquid phase reaction for the lower aldehydes pressures up to a few thousand psig may be employed, especially at higher reaction temperatures, but as the molecular weight of the aldehyde increases lower pressures are needed to ensure complete liquid phase reaction. It will be readily appreciated that the appropriate pressure necessary to maintain a liquid phase throughout the reactor can be readily determined by one skilled in the art and will depend on the feedstock molecular weight and reaction temperature, as stated above. The liquid hourly space velocity, or the feed rate of reactant, is not critical to the success of this invention but is rather a variable which is optimized with respect to productivity. For example, it has been found that liquid hourly space velocities on the order of 2–10 form a convenient range within which to work. But it is to be emphasized that these are not limiting figures but are rather only illustrative of the characteristics of the process carried out according to out invention.

As previously noted, 2-ethyl-2-hexenal is particularly important in the preparation of 2-ethylhexanol-1 by selective hydrogenation of the olefinic center in the unsaturated aldehyde, and it is possible to devise a process where aldol condensation, dehydration of the aldol product, and hydrogenation of the olefinic center occur concurrently in the same catalyst bed. For example, metals having selective olefinic hydrogenation activity relative to an aldehydic moiety can be deposited largely in the interior of catalyst particles previously described to afford a metal-modified catalyst. Feedstock subsequently can be contacted with the metal-modified catalyst in the presence of hydrogen at pressures of 50 up to 1000 psig, and at temperatures between about 80° C. and about 200° C., conditions which effect consecutively aldol condensation, dehydration of the aldol product, and hydrogenation of the olefinic center without causing hydrogenation of the aldehyde moiety to any substantial degree. Alternatively, one can prepare as a solid solution of magnesium oxide and aluminum oxide a catalyst of the type described above where some of the magnesium is replaced by a divalent metal cation M(II) which, under its conditions of use, is partially reduced to the zerovalent metal, M(0), having selective olefinic hydrogenation activity relative to an aldehydic moiety and behaves under reaction conditions to selectively catalyze reduction of the olefinic center. Example of metals which may be used include platinum, iridium, osmium, palladium, rhenium, ruthenium, rhodium, and nickel, where palladium and nickel are especially preferred metals in this variant of our invention. In both cases the resulting process is one where an aldehyde of this invention, such as butyraldehyde, is the feedstock along with hydrogen and a saturated alcohol with twice as many carbons as the aldehyde is the product, as exemplified by 2-ethylhexanol-1.

The preparation of extrudates having a skewed metal distribution is known to a person of ordinary skill to result either in a product having the metal concentrated in a core at the center of the extrudate, or alternatively in a circular "shell" around a core of the support in which the metal is impregnated. M. Komiyama, *Catalysis Reviews, Science and Engineering*, V. 27, 341 (1985). One could prepare as a catalyst a support of a solid solution of magnesium oxide and aluminum oxide by either method where the metal impregnating the support has selective olefinic hydrogenation activity relative to an aldehydic moiety. Prime examples of metals, particularly in the zerovalent state, commonly used to catalyze hydrogenation include the Group VIII metals of platinum, palladium, nickel, rhodium, rhenium, iridium, and osmium. In many cases a combination of metals is used, both combinations of Group VIII metals alone as well as one or more Group VIII metals with metals such as cobalt, iron, copper, and so on. Whatever the method of preparing an extrudate with a skewed metal distribution, the initial aldol condensation and aldol product dehydration would occur largely in the metal-free portion of the catalyst, and subsequent diffusion of the latter product, as e.g. 2-ethyl-2-hexenal, into the metal portion would result in selective reduction of the olefinic linkage under the reaction conditions.

The other alternative is to prepare two different kinds of hydrotalcite-like materials, one only with Mg and Al, the other where Mg is replaced by a metal effective to catalyze olefin reduction, as for example nickel, palladium, platinum, rhodium, rhenium, ruthenium, indium, and osmium, particularly nickel and palladium. It is most preferred that the Mg/Al and M/Al ratios be the same, where M is the other metal replacing magnesium in the hydrotalcite-like material. The separate materials could be coextruded using a double dye, the finished dough dried and calcined as previously described, to afford the final catalyst.

The following examples are only illustrative of our invention and do not limit it in any way. Other embodiments and variants will be apparent to one of ordinary skill in the art.

EXAMPLE 1

Catalyst preparation. A 2L, 3-necked round bottomed flask was equipped with an addition funnel, a thermometer, a mechanical stirrer, and a heating mantle. To this flask was added a solution containing 610 g of water, 60 g of $Na_2CO_3.H_2O$ and 71 g of NaOH and the contents were cooled to $<5°$ C. The addition funnel was charged with a solution of 345 g water, 77 g $Mg(NO_3)_2.6H_2O$ and 75 g $Al(NO_3)_3.9H_2O$ and this solution was added over a period of 4 hours. The solution temperature was maintained at $<5°$ C. throughout the addition and the resulting slurry was stirred for 1 hour at $<5°$ C. The addition funnel was replaced by a reflux condenser and the slurry was heated to $60°\pm5°$ C. for 1 hour. The slurry was then cooled to room temperature and the solids recovered by filtration. The solids were washed with 10L of hot deionized water. The solids were then dried at 100° C. for 16 hours and this product was characterized as hydrotalcite by its x-ray diffraction (XRD) pattern. After crushing, the solid was calcined at 450° C. for 12 hours in a muffle furnace with an air flow. This product was characterized as a $MgO-Al_2O_3$ solid solution (Mg/Al=1.5) by XRD. The BET surface area for this material was 285 $m^2/g$. Materials with a different Mg/Al ratio may be prepared by similar means, changing only the relative molar ratio of $Mg(NO_3)_2.6H_2O$ and $Al(NO_3)_3.H_2O$.

EXAMPLE 2

General method of continuous aldol condensation. The reactor consisted of a feed vessel containing, for example, butyraldehyde as the feedstock, a feed pump for charging the feedstock to the reactor, and the reactor section which was a vertical ⅜ inch ID stainless steel pipe approximately 3 feet in length fitted with a spiral preheater in the lower section of the pipe. The reactor was housed inside a tube furnace and a thermocouple probe extended into the center of the reactor to afford a direct measurement of reaction temperature in the catalyst zone. Five grams of the solid solution of magnesium oxide-aluminum oxide to be tested was mixed with an equal volume of sand and loaded into the reactor above the preheater, with the sand provided to afford improved liquid flow characteristics through the catalyst bed to reduce the likelihood of channeling. The catalyst bed depth was approximately 6 inches. Effluent was collected and analyzed by gas chromatography using a 50 m×0.2 mm ID×0.5 micron methylsilicone film. The instrument was temperature programmed from 50° to 240° C. at 8° C. per minute and held at 240° C. for 10 minutes.

Test runs were initiated using the following procedure. The catalyst bed was treated in the reactor at 500° C. under flowing nitrogen 2 hours and then cooled to room temperature. With butyraldehyde as the reactant, the feedstock was pumped upflow at 150 grams per hour through the bottom of the reactor with the reactor pressure maintained at 1500 psig. The reactor was then heated to reaction temperature, and when the reactor was liquid full the feed rate was decreased to 50 grams per hour and maintained at that rate.

Typical results for butyraldehyde as the feedstock are presented in Table 1 which show the extent of reaction (conversion) and selectivity of 2-ethyl-2-hexenal formation as a function of temperature using as a catalyst material with Mg/Al=1.5 as prepared according to Example 1. Table 2 presents a summary of these results, giving average values of conversion and selectivity at various temperatures.

TABLE 1

| | | Reaction of Butyraldehyde | | | |
|---|---|---|---|---|---|
| Time (hrs) | Temperature °C. | % Butyraldehyde | % 2-Ethyl-2-hexenal | Conversion, percent | % Selectivity percent |
| 19 | 100 | 88.21 | 2.15 | 11.79 | 18.22 |
| 22 | 100 | 85.25 | 2.48 | 14.75 | 16.80 |
| 25 | 100 | 87.62 | 2.30 | 12.38 | 18.57 |
| 28 | 100 | 89.26 | 1.76 | 10.74 | 16.38 |
| 31 | 100 | 90.30 | 1.74 | 9.70 | 17.91 |
| 34 | 100 | 90.35 | 1.41 | 9.65 | 14.56 |
| 37 | 100 | 90.28 | 1.49 | 9.72 | 15.28 |
| 40 | 100 | 90.66 | 1.67 | 9.34 | 17.85 |
| 47 | 120 | 49.38 | 36.35 | 50.62 | 71.81 |
| 50 | 120 | 52.01 | 34.99 | 47.99 | 72.92 |
| 53 | 120 | 54.74 | 32.54 | 45.26 | 71.90 |
| 56 | 140 | 42.10 | 47.28 | 57.90 | 81.65 |
| 59 | 140 | 45.71 | 45.14 | 54.30 | 83.13 |
| 62 | 140 | 37.47 | 50.03 | 62.53 | 80.01 |
| 66 | 140 | 33.93 | 54.88 | 66.08 | 83.05 |
| 69 | 140 | 32.79 | 56.45 | 67.21 | 83.99 |
| 72 | 140 | 34.21 | 54.06 | 65.79 | 82.18 |
| 75 | 140 | 34.61 | 53.55 | 65.39 | 81.90 |
| 79 | 160 | 25.44 | 59.99 | 74.56 | 80.45 |
| 82 | 160 | 23.66 | 61.43 | 76.34 | 80.47 |
| 85 | 160 | 25.58 | 60.76 | 74.42 | 81.65 |
| 88 | 160 | 27.47 | 60.59 | 72.53 | 83.54 |
| 91 | 160 | 27.58 | 61.04 | 72.42 | 84.29 |
| 94 | 160 | 26.84 | 60.11 | 73.17 | 82.15 |
| 97 | 160 | 25.10 | 61.76 | 74.90 | 82.46 |
| 101 | 180 | 15.39 | 69.29 | 84.62 | 81.89 |
| 104 | 180 | 16.50 | 67.88 | 83.50 | 81.30 |
| 108 | 180 | 19.46 | 65.08 | 80.54 | 80.81 |
| 111 | 180 | 17.88 | 67.35 | 82.13 | 82.01 |
| 114 | 180 | 14.33 | 69.85 | 85.67 | 81.53 |
| 117 | 180 | 20.00 | 64.39 | 80.00 | 80.49 |
| 120 | 180 | 19.75 | 65.05 | 80.25 | 81.06 |
| 123 | 180 | 17.54 | 66.47 | 82.46 | 80.61 |
| 126 | 180 | 16.15 | 66.83 | 83.85 | 79.71 |
| 129 | 180 | 18.95 | 63.92 | 81.05 | 78.87 |
| 132 | 180 | 15.64 | 67.39 | 84.36 | 79.88 |
| 135 | 180 | 20.38 | 63.69 | 79.62 | 80.00 |
| 138 | 180 | 19.45 | 65.28 | 80.55 | 81.05 |
| 141 | 180 | 20.61 | 64.00 | 79.39 | 80.61 |
| 144 | 180 | 22.79 | 62.39 | 77.22 | 80.80 |
| 147 | 180 | 24.77 | 61.74 | 75.24 | 82.07 |
| 151 | 190 | 23.81 | 61.93 | 76.19 | 81.28 |
| 154 | 190 | 16.62 | 67.26 | 83.38 | 80.67 |
| 157 | 190 | 21.59 | 62.06 | 78.41 | 79.16 |
| 160 | 190 | 23.65 | 61.55 | 76.35 | 80.62 |
| 163 | 190 | 21.22 | 64.83 | 78.78 | 82.29 |
| 166 | 190 | 25.92 | 60.69 | 74.08 | 81.92 |
| 169 | 190 | 20.38 | 64.66 | 79.63 | 81.20 |

TABLE 2

| | Average Conversion and Selectivity | |
|---|---|---|
| Temperature (°C) | Conversion, percent | Selectivity, percent |
| 100 | 11.6 | 16.1 |
| 120 | 48.0 | 72.3 |
| 140 | 64.0 | 82.2 |
| 160 | 75.1 | 82.6 |
| 180 | 89.0 | 80.7 |
| 190 | 70.7 | 81.2 |

The foregoing shows that conversion of close to 90% can be obtained and that selectivity of 2-ethyl-2-hexenal formation in excess of 80% is routine.

EXAMPLE 3

The following may be conducted in a continuous fixed bed system consisting of a liquid feed charger and pump, a hydrogen feed system, a 1" ID vertical tube reactor with furnace, and a gas-liquid separator. The catalyst may be, for example, 1% Pd supported on a solid solution of $Al_2O_3$-MgO in such a manner that the Pd resides only in the interior of each catalyst particle. Ten grams of this catalyst may be placed into the reactor below a spiral preheater and fixed in place so that it maintains its position during flow operation. A neat butyraldehyde feed may be charged upflow continuously to the reactor at 30 g/hr. Hydrogen flow may be started upflow to the reactor at a 4:1 mole ratio of $H_2$ to butyraldehyde at 200 psig reactor pressure and the reactor temperature may be brought to 150° C. Within the reactor, aldol condensation of butyraldehyde to 2-ethyl-2-hexenal and hydrogenation to 2-ethylhexanol occur consecutively over the same catalyst bed. Butyraldehyde conversion of 90% with 75% selectivity to 2-ethylhexanol-1 may be achieved.

What is claimed is:

1. A process for preparing 2-ethylhexanol-1 comprising flowing butyraldehyde over a catalyst at a temperature from about 80° to about 200° C. at a hydrogen partial pressure from about 50 to about 1000 pounds per square inch, said catalyst consisting essentially of a solid solution of magnesium oxide and aluminum oxide with a surface area from about 250 to about 350 m²/g impregnated with a metal which selectively hydrogenates an olefinic moiety relative to an aldehydic moiety, said metal being deposited in an amount effective to catalyze the hydrogenation of said olefinic moiety.

2. The process of claim 1 where the catalyst has a surface area from about 275 to about 350 m²/g.

3. The process of claim 2 where the surface area is between about 300 and about 350 m²/g.

4. The process of claim 1 where the number atom ratio of Mg/Al in the catalyst is from about 1.5 to about 2.5.

5. The process of claim 1 where the reaction temperature is from about 100° to about 190° C.

6. The process of claim 1 where the mass of n-butyraldehyde flowing through the fixed mass of catalyst is in the liquid phase.

7. The process of claim 1 further characterized by a reaction pressure sufficient to maintain the n-butyraldehyde in the liquid phase.

8. The process of claim 1 where the metal is selected from the group consisting of platinum, palladium, nickel, rhodium, rhenium, ruthenium, iridium, and osmium.

9. The process of claim 8 where the metal is nickel or palladium.

10. The process of claim 1 further characterized in that the catalyst has a skewed metal distribution where the metal is concentrated in a central core.

11. The process of claim 1 further characterized in that the catalyst has a skewed metal distribution where the metal is concentrated in a circular shell around a core of the solid solution.

12. A process for preparing 2-ethylhexanol-1 comprising flowing butyraldehyde over a catalyst at a temperature from about 80° to about 200° C. at a hydrogen partial pressure from about 50 to about 1000 pounds per square inch, said catalyst consisting essentially of a mixture of solid solutions of a) magnesium oxide and aluminum oxide and b) a second divalent metal oxide and aluminum oxide having a surface area from about 250 to about 350 m²/g.

13. The process of claim 12 where the catalyst has a surface area from about 275 to about 350 m²/g.

14. The process of claim 13 where the surface area is between about 300 and about 350 m²/g.

15. The process of claim 13 where the number atom ratio of Mg/Al in the solid solution of magnesium oxide and aluminum oxide is from about 1.5 to about 2.5.

16. The process of claim 13 where the reaction temperature is from about 100° to about 190° C.

17. The process of claim 13 where the mass of n-butyraldehyde flowing through the fixed mass of basic catalyst is in the liquid phase.

18. The process of claim 13 further characterized by a reaction pressure sufficient to maintain the n-butyraldehyde in the liquid phase.

19. The process of claim 10 where said second divalent metal is selected from the group consisting of platinum, palladium, nickel, rhodium, rhenium, ruthenium, iridium, and osmium.

20. The process of claim 10 where said second divalent metal is nickel or palladium.

* * * * *